US009770243B2

(12) United States Patent
Wang et al.

(10) Patent No.: US 9,770,243 B2
(45) Date of Patent: Sep. 26, 2017

(54) HANDLE FOR ELECTRIC SURGICAL STAPLER

(71) Applicant: B. J. ZH. F. Panther Medical Equipment Co., Ltd., Beijing (CN)

(72) Inventors: Shuxin Wang, Tianjin (CN); Jianchen Wang, Tianjin (CN); Xuejun Li, Beijing (CN); Qing Liu, Beijing (CN)

(73) Assignee: B. J. ZH. F. PANTHER MEDICAL EQUIPMENT CO., LTD., Beijing (CN)

( * ) Notice: Subject to any disclaimer, the term of this patent is extended or adjusted under 35 U.S.C. 154(b) by 407 days.

(21) Appl. No.: 14/561,236

(22) Filed: Dec. 5, 2014

(65) Prior Publication Data

US 2015/0083777 A1 Mar. 26, 2015

Related U.S. Application Data

(63) Continuation-in-part of application No. PCT/CN2013/000938, filed on Aug. 9, 2013.

(30) Foreign Application Priority Data

Jan. 29, 2013 (CN) .......................... 2013 1 0032640

(51) Int. Cl.
*A61B 17/04* (2006.01)
*A61B 17/10* (2006.01)
*A61B 17/068* (2006.01)
*A61B 17/072* (2006.01)
*A61B 17/115* (2006.01)
*A61B 17/00* (2006.01)
*A61B 17/29* (2006.01)

(52) U.S. Cl.
CPC .......... *A61B 17/068* (2013.01); *A61B 17/072* (2013.01); *A61B 17/07207* (2013.01); *A61B 17/115* (2013.01); *A61B 2017/0046* (2013.01); *A61B 2017/00115* (2013.01); *A61B 2017/00398* (2013.01); *A61B 2017/2919* (2013.01); *A61B 2017/2925* (2013.01)

(58) Field of Classification Search
CPC ............ A61B 2019/464; A61B 17/068; A61B 17/1707; A61B 2019/5259
USPC ........................................... 227/175.1–182.1
See application file for complete search history.

(56) References Cited

U.S. PATENT DOCUMENTS 5,312,024 A * 5/1994 Grant .................... A61B 17/115
227/179.1
5,391,166 A * 2/1995 Eggers ............... A61B 18/1206
606/170
5,474,223 A * 12/1995 Viola .................... A61B 17/072
227/175.1
5,782,397 A * 7/1998 Koukline ........... A61B 17/0686
227/119

(Continued)

*Primary Examiner* — Robert Long
(74) *Attorney, Agent, or Firm* — Matthias Scholl, PC; Matthias Scholl

(57) ABSTRACT

A handle for an electric surgical stapler. The electric surgical stapler includes an end effector. The handle includes a casing, a linear motor, a power transmission mechanism, and a quick change interface. The linear motor is disposed in the casing and configured to supply linear motion. The power transmission mechanism transmits the linear motion from the linear motor to the end effector. The quick change interface is connected to the end effector.

10 Claims, 10 Drawing Sheets

(56) References Cited

U.S. PATENT DOCUMENTS

| | | | | |
|---|---|---|---|---|
| 5,954,535 A * | 9/1999 | Lawrence | ............ | H01R 4/4836 439/439 |
| 5,971,801 A * | 10/1999 | Kato | .................... | B60L 3/0069 439/157 |
| 6,443,973 B1 * | 9/2002 | Whitman | ......... | A61B 17/07207 227/176.1 |
| 6,727,477 B1 * | 4/2004 | Li-Chen | .................. | G01K 1/14 219/481 |
| 6,988,897 B2 * | 1/2006 | Belongia | ............ | H01R 13/6205 219/481 |
| 7,422,136 B1 * | 9/2008 | Marczyk | .......... | A61B 17/07207 227/175.1 |
| 7,721,930 B2 * | 5/2010 | McKenna | ........ | A61B 17/00491 227/175.1 |
| 7,721,931 B2 * | 5/2010 | Shelton, IV | ..... | A61B 17/07207 227/176.1 |
| 7,743,960 B2 * | 6/2010 | Whitman | ......... | A61B 17/07207 227/175.1 |
| 7,922,063 B2 * | 4/2011 | Zemlok | ............ | A61B 17/07207 227/175.1 |
| 8,628,467 B2 * | 1/2014 | Whitman | ............ | A61B 10/0233 600/129 |
| 8,827,134 B2 * | 9/2014 | Viola | ............... | A61B 17/07207 227/176.1 |
| 8,862,209 B2 * | 10/2014 | Whitman | .................. | A61B 1/05 600/407 |
| 2001/0031975 A1 * | 10/2001 | Whitman | ............ | A61B 10/0233 606/167 |
| 2002/0050366 A1 * | 5/2002 | Driessen | .................... | B25F 3/00 173/216 |
| 2005/0125027 A1 * | 6/2005 | Knodel | .................. | A61B 17/29 606/205 |
| 2005/0272565 A1 * | 12/2005 | Hao | .................... | A63B 22/0235 482/54 |
| 2007/0023477 A1 * | 2/2007 | Whitman | ......... | A61B 17/07207 227/175.1 |
| 2008/0242510 A1 * | 10/2008 | Topel | ................. | A63B 22/0235 482/4 |
| 2008/0275471 A1 * | 11/2008 | Viola | .................... | A61B 17/128 606/142 |
| 2008/0308601 A1 * | 12/2008 | Timm | ............... | A61B 17/07207 227/175.1 |
| 2009/0054208 A1 * | 2/2009 | Wu | .................... | A63B 22/0235 482/4 |
| 2009/0254094 A1 * | 10/2009 | Knapp | ................ | A61B 17/1637 606/96 |
| 2011/0022032 A1 * | 1/2011 | Zemlok | ............ | A61B 17/07207 606/1 |
| 2011/0095067 A1 * | 4/2011 | Ohdaira | ............... | A61B 17/115 227/175.2 |
| 2011/0125138 A1 * | 5/2011 | Malinouskas | ........ | A61B 17/068 606/1 |
| 2011/0174099 A1 * | 7/2011 | Ross | .................... | A61B 17/072 74/89.32 |
| 2012/0061447 A1 * | 3/2012 | Williams | ............. | A61B 17/115 227/175.1 |
| 2012/0089131 A1 * | 4/2012 | Zemlok | ............ | A61B 17/07207 606/1 |
| 2012/0116388 A1 * | 5/2012 | Houser | ............ | A61B 17/00234 606/41 |
| 2012/0199632 A1 * | 8/2012 | Spivey | ............. | A61B 17/07207 227/176.1 |
| 2012/0209317 A1 * | 8/2012 | Oepen | ................ | A61B 17/0057 606/213 |
| 2013/0020106 A1 * | 1/2013 | Kuehne | ..................... | B25F 5/02 173/214 |
| 2013/0098966 A1 * | 4/2013 | Kostrzewski | .... | A61B 17/07207 227/176.1 |
| 2013/0131650 A1 * | 5/2013 | Whitman | ........... | A61B 10/0233 606/1 |
| 2013/0324979 A1 * | 12/2013 | Nicholas | ............... | A61B 17/068 606/1 |
| 2014/0001236 A1 * | 1/2014 | Shelton, IV | ..... | A61B 17/07207 227/176.1 |
| 2014/0025046 A1 * | 1/2014 | Williams | ......... | A61B 17/07207 606/1 |
| 2014/0207166 A1 * | 7/2014 | Shelton, IV | ..... | A61B 17/07207 606/170 |
| 2014/0236173 A1 * | 8/2014 | Scirica | ............. | A61B 17/07207 606/130 |
| 2014/0236174 A1 * | 8/2014 | Williams | ......... | A61B 17/00234 606/130 |
| 2014/0246478 A1 * | 9/2014 | Baber | .................. | A61B 17/068 227/180.1 |
| 2014/0276776 A1 * | 9/2014 | Parihar | .................. | A61B 17/28 606/41 |
| 2015/0014393 A1 * | 1/2015 | Milliman | ............ | A61B 90/98 227/180.1 |
| 2015/0048140 A1 * | 2/2015 | Penna | ................. | A61B 17/068 227/176.1 |
| 2015/0053749 A1 * | 2/2015 | Shelton, IV | ......... | A61B 17/068 227/181.1 |
| 2015/0216525 A1 * | 8/2015 | Collins | .................... | H05K 7/06 227/176.1 |
| 2015/0343583 A1 * | 12/2015 | McRoberts | ............ | B23Q 5/045 173/213 |
| 2016/0166249 A1 * | 6/2016 | Knodel | ............ | A61B 17/07207 227/177.1 |
| 2016/0242779 A1 * | 8/2016 | Aranyi | ............ | A61B 17/07207 |

\* cited by examiner

HANDLE FOR ELECTRIC SURGICAL STAPLER

CROSS-REFERENCE TO RELATED APPLICATIONS

This application is a continuation-in-part of International Patent Application No. PCT/CN2013/000938 with an international filing date of Aug. 9, 2013, designating the United States, now pending, and further claims priority benefits to Chinese Patent Application No. 201310032640.6 filed Jan. 29, 2013. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18$^{th}$ Floor, Cambridge, Mass. 02142.

BACKGROUND OF THE INVENTION

Field of the Invention

The invention relates to a handle for an electric surgical stapler.

Description of the Related Art

A typical manual surgical stapler is complex in design, yet the staple lines it produces are often not accurate and not adapted in strength to the different patients and tissues being stapled. In addition, the surgical stapler is often disposable because its complexity prevents adequate sterilization.

SUMMARY OF THE INVENTION

In view of the above-mentioned problems, it is an objective of the invention to provide an improved handle for an electric surgical stapler.

The handle can be applied to different end effectors.

To achieve the above objective, in accordance with one embodiment of the invention, there is provided a handle for an electric surgical stapler, the electric surgical stapler comprising an end effector, the handle comprising a casing, a linear motor, a power transmission mechanism, and a quick change interface. The linear motor is disposed in the casing and configured to supply linear motion. The power transmission mechanism transmits the linear motion from the linear motor to the end effector. The quick change interface is connected to the end effector.

In a class of this embodiment, the power transmission mechanism comprises a driving flexible shaft, and the linear motion from the linear motor is transmitted to the end effector via the driving flexible shaft.

In a class of this embodiment, a drive module is disposed between the linear motor and the driving flexible shaft, and the linear motion from the linear motor is transmitted to the driving flexible shaft via the drive module.

In a class of this embodiment, the drive module comprises a universal joint assembly, a drive shaft, and a coupling; the universal joint assembly comprises a first universal joint, a second universal joint, and a connection rod; an output shaft of the linear motor is connected to the first universal joint, the first universal joint is connected to the connection rod, and the connection rod is connected to the second universal joint; the second universal joint is connected to the drive shaft; and the drive shaft is connected to the driving flexible shaft via the coupling.

In a class of this embodiment, the drive module comprises a gear mechanism and a drive shaft; the linear motor is connected to the gear mechanism, the gear mechanism is connected to the drive shaft, and the drive shaft is connected to the driving flexible shaft.

In a class of this embodiment, the drive module comprises a flexible shaft and a drive shaft; the linear motor is connected to the flexible shaft, the flexible shaft is connected to the drive shaft, and the drive shaft is connected to the driving flexible shaft.

In a class of this embodiment, the handle further comprises a connection tube, one end of the connection tube is fixed on the casing, the other end thereof is connected to the quick change interface; and the driving flexible shaft is disposed in the connection tube.

In a class of this embodiment, the connection tube is semirigid, and exhibits a certain bending deflection and rigidity under stress.

In a class of this embodiment, the connection tube comprises an end joint, the quick change interface comprises a fixed seat for the end joint, a precession sleeve, and an output head; the end joint is fixed on the connection tube; the fixed seat is fixed on the end joint of the connection tube; the precession sleeve is fixed between the fixed seat and the end joint, and is axially fixed and circumferentially rotatable; and the output head is disposed in the fixed seat, and is axially fixed and circumferentially rotatable; one end of the output head is connected to the drive flexible shaft, and the other end thereof is connected to a transmission mechanism of the end effector.

In a class of this embodiment, the quick change interface comprises a threaded connector, a snap spring, and a slip groove.

In a class of this embodiment, the electric surgical stapler is a linear stapler, circular anastomat, endoscopic stapler, or knife stapler.

Advantages of the invention according to embodiments of the invention are summarized as follows:

1. The handle is driven by a motor, thereby preventing inaccuracies resulting from manual operation, and improving the chances of successful surgeries;

2. The handle comprises a normal quick change interface adapted to different end effectors for stapling, anastomosing, and cutting-stapling human or animal tissues, so it is economic and convenient;

3. The handle is easily sterilized and reusable, so the utilization rate is improved, the costs is reduced, which is beneficial to environmental protection; and 4. The connection tube of the handle is semirigid, so that the bending angle is adjustable for adapting to different surgical situations.

DETAILED DESCRIPTION OF THE EMBODIMENTS

The handle of the invention can be applied to different end effectors such as linear staplers, circular anastomats, endoscopic staplers, and knife staplers, to form an electric surgical stapler for stapling, anastomosing, and cutting-stapling human or animal tissues.

Figure 1:
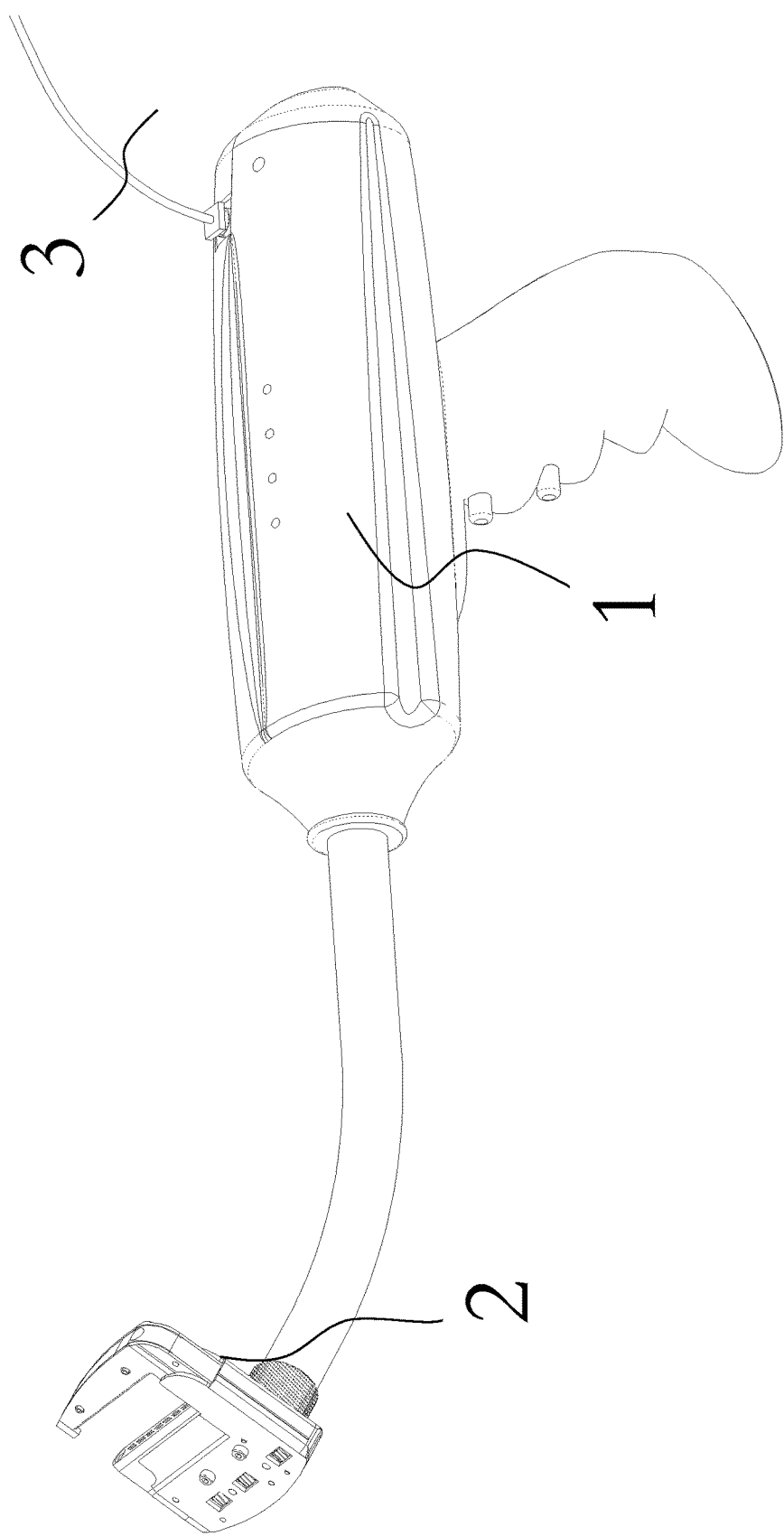
FIG. 1 is a schematic diagram showing a connection of a handle and an end effector of a linear stapler according to one embodiment of the invention.
Figure 2:
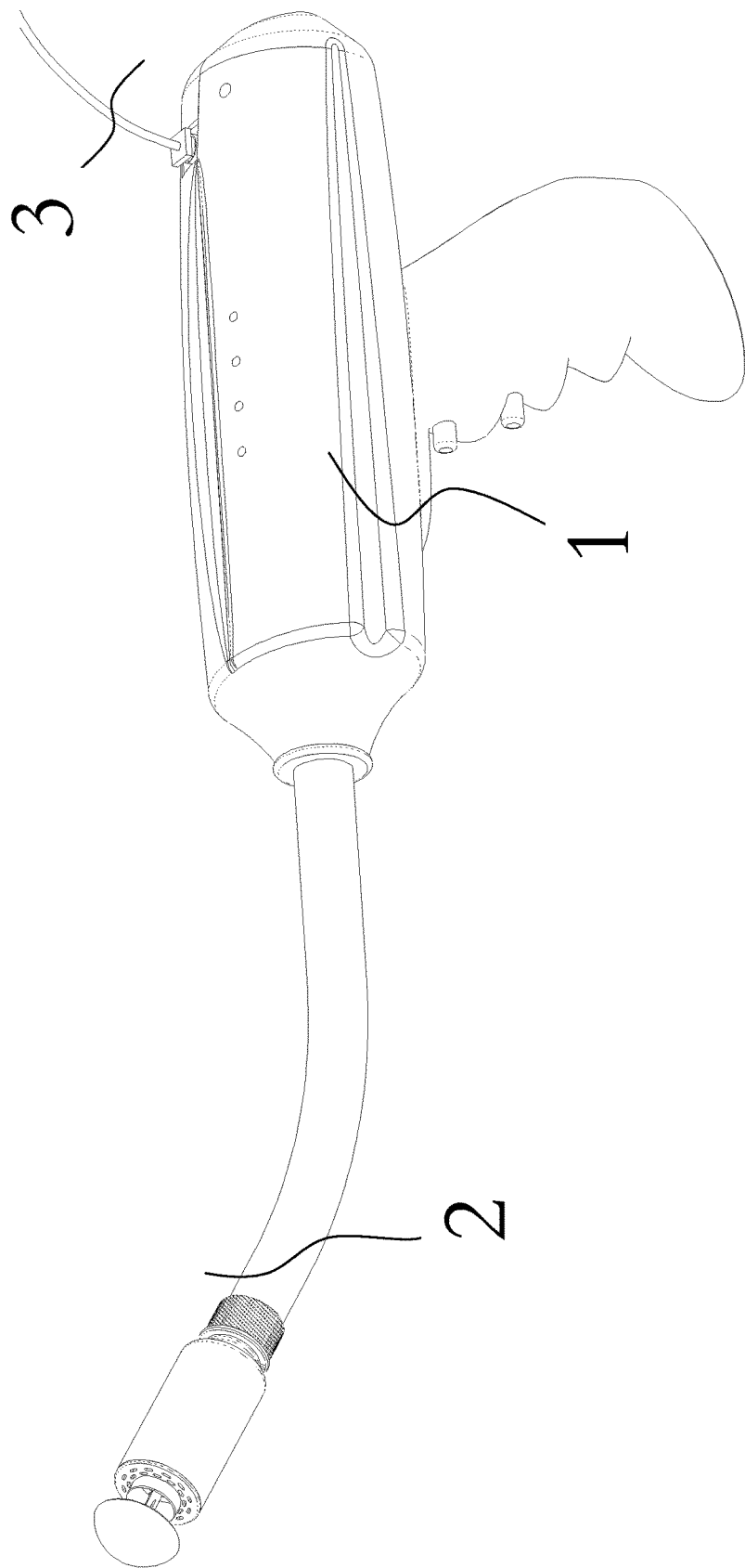
FIG. 2 is a schematic diagram showing a connection of a handle and an end effector of a circular anastomat according to one embodiment of the invention.
Figure 3:
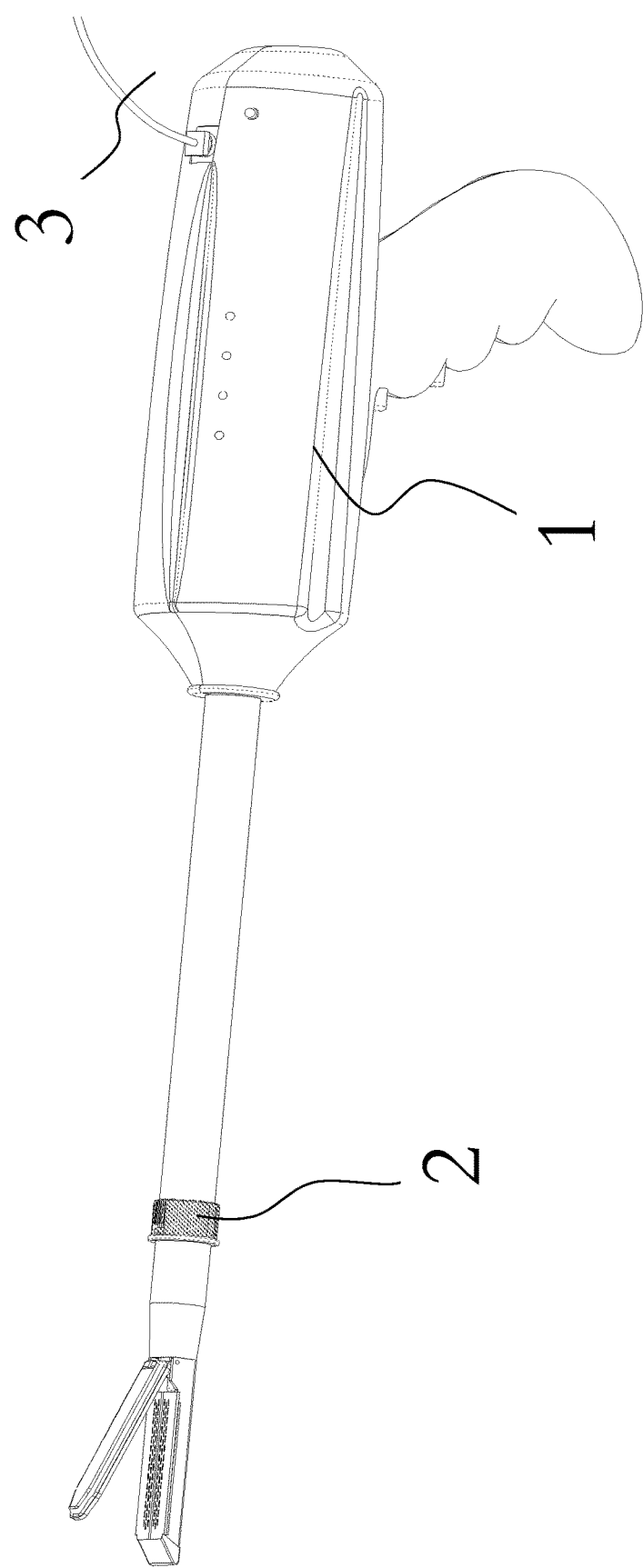
FIG. 3 is a schematic diagram showing a connection of a handle and an end effector of an endoscopic stapler according to one embodiment of the invention.

FIG. 1 is a schematic diagram showing the connection of the handle and an end effector of a linear stapler. FIG. 2 is a schematic diagram showing the connection of the handle and an end effector of a circular anastomat. FIG. 3 is a schematic diagram showing the connection of the handle and an end effector of an endoscopic stapler.

As shown in FIGS. 1-3, an electric surgical stapler comprises the handle 1, an end effector 2, and a control assembly 3.

Figure 4:
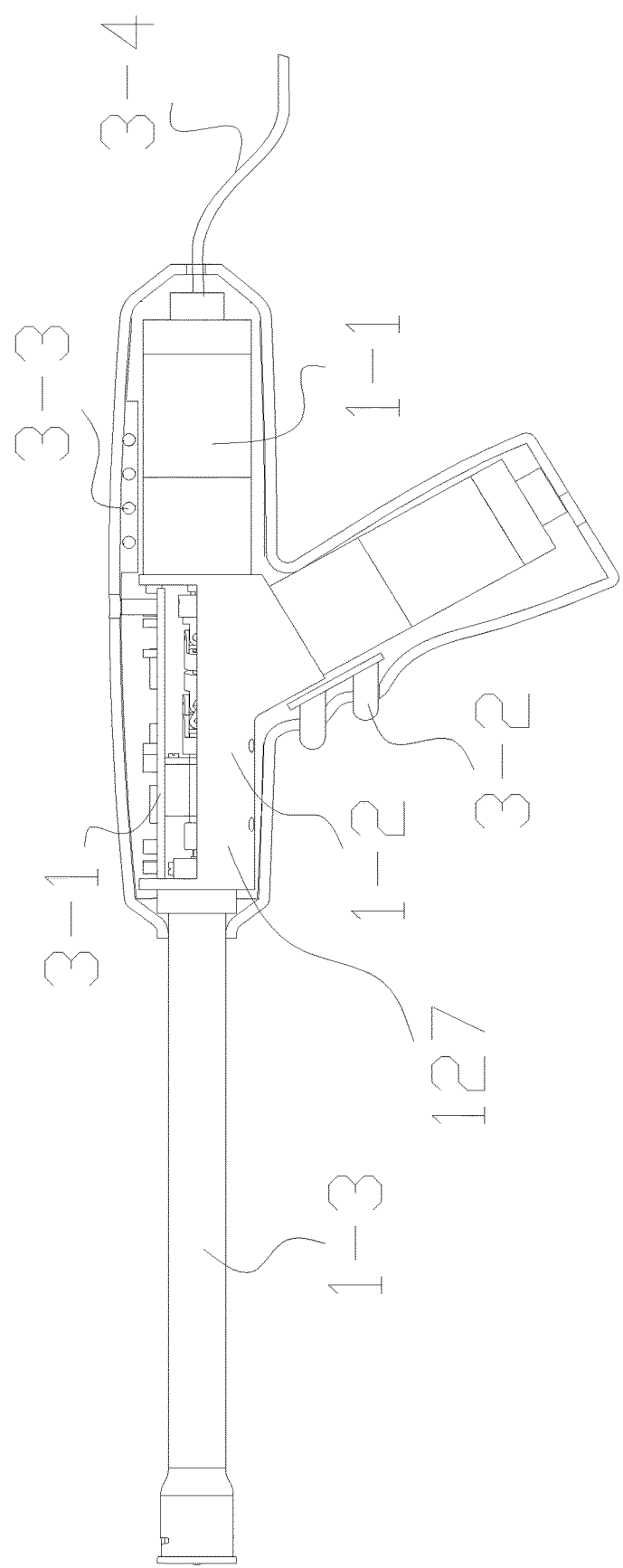
FIG. 4 is a schematic diagram of a handle according to one embodiment of the invention.

FIG. 4 is a schematic diagram of a handle.

As shown in FIG. 4, the handle comprises a linear motor 1-1, a power transmission mechanism 1-2, a connection tube, and a quick change interface 1-3. The control assembly 3 comprises a control circuit board 3-1, a control button 3-2, an indicator light 3-3, and a DC power supply 3-4. The power supply can be a built-in power supply, for example, batteries. The linear motor 1-1 is fixed on a main frame 127 using a bolt or by bonding. The linear motor 1-1 is a brush DC motor or a brushless DC motor. Two motors are provided and arranged in one plane, and there is an angle between the output shafts thereof. The output shafts of the motors are connected to the power transmission mechanism 1-2. The power transmission mechanism 1-2 transforms two angled power outputs into a pair of parallel rotation outputs, which are used to drive the end effector to act. The main transmission components are disposed in the main frame 127. The connection tube 1-3 is fixed on the main frame 127. The connection tube can pass through a round hole of the main frame and fixed thereon by screws or pins. The control circuit board 3-1 is fixed on the power transmission mechanism 1-2, specifically, is fixed on a bearing support 125. Optionally, the control circuit board can be fixed by other modes. The control button 3-2 and the indicator light 3-3 are disposed on the casing. The control button is disposed at the grip of the handle. The indicator light is disposed at the upper part of the casing. Different combinations of the control buttons can achieve different actions of the electric stapler. The indicator light can exhibit different indicator signals for different actions.

Figure 5:
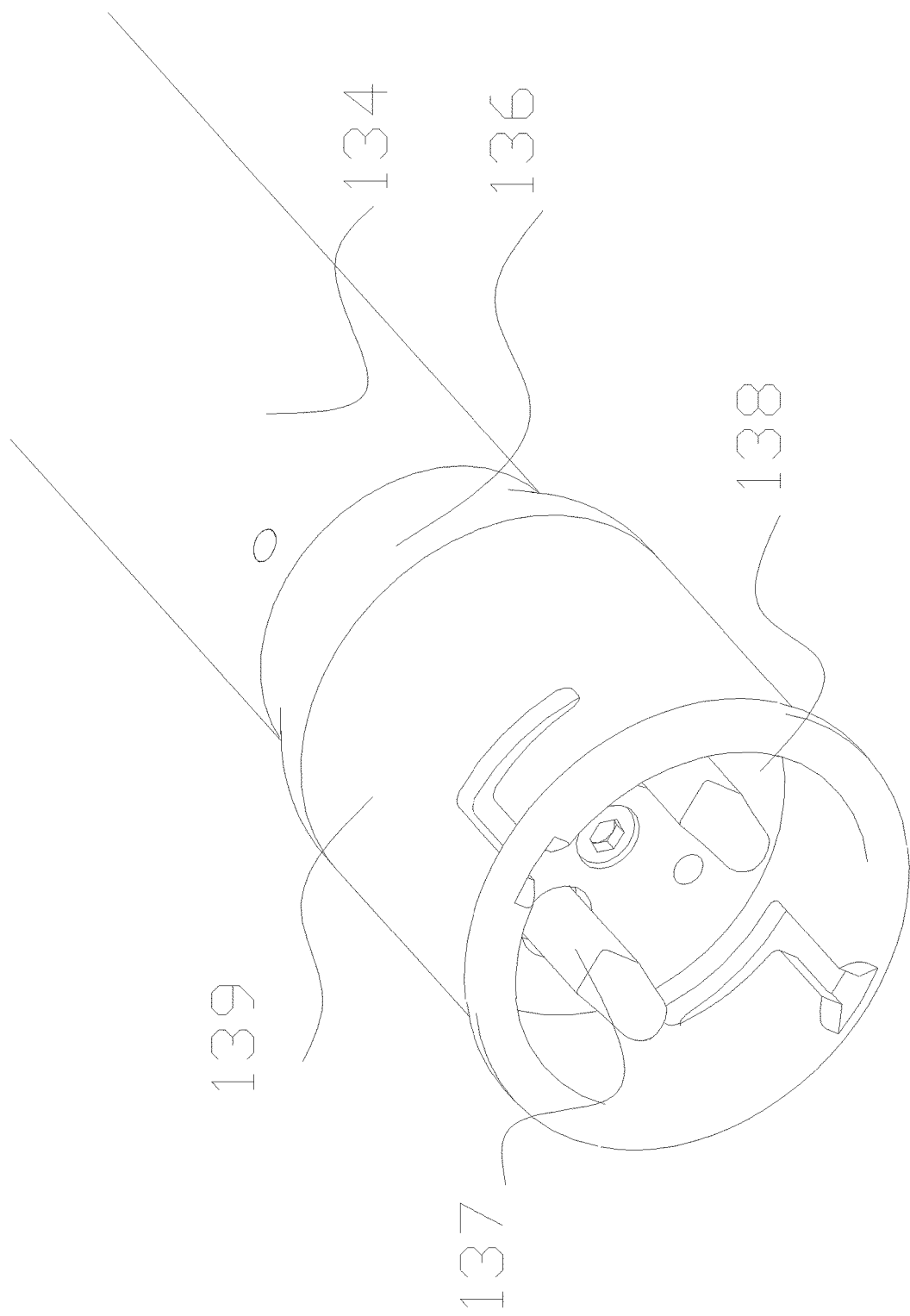
FIG. 5 is a schematic diagram of a quick change interface of a handle according to one embodiment of the invention.

FIG. 5 is a schematic diagram of the quick change interface of the handle.

As shown in FIG. 5, the handle is connected to an end effector via the quick change interface, including but not limited to a terminal of a linear stapler, circular anastomat, endoscopic stapler, or knife stapler. The connection tube 134 comprises an end joint 136 which is fixed on the connection tube using a pin or tight fit. A fixed seat 138 for the end joint is fixed on the end joint 136 via a screw and a circumferential locating pin. The precession sleeve 139 and the fixed seat 138 interact by clearance fit. The fixed seat 138 enables the precession sleeve 139 to be fixed axially. However, the precession sleeve can rotate circumferentially. An output head 137 of the handle is disposed inside the fixed seat 138, and is fixed axially but rotatable circumferentially.

Figure 6:
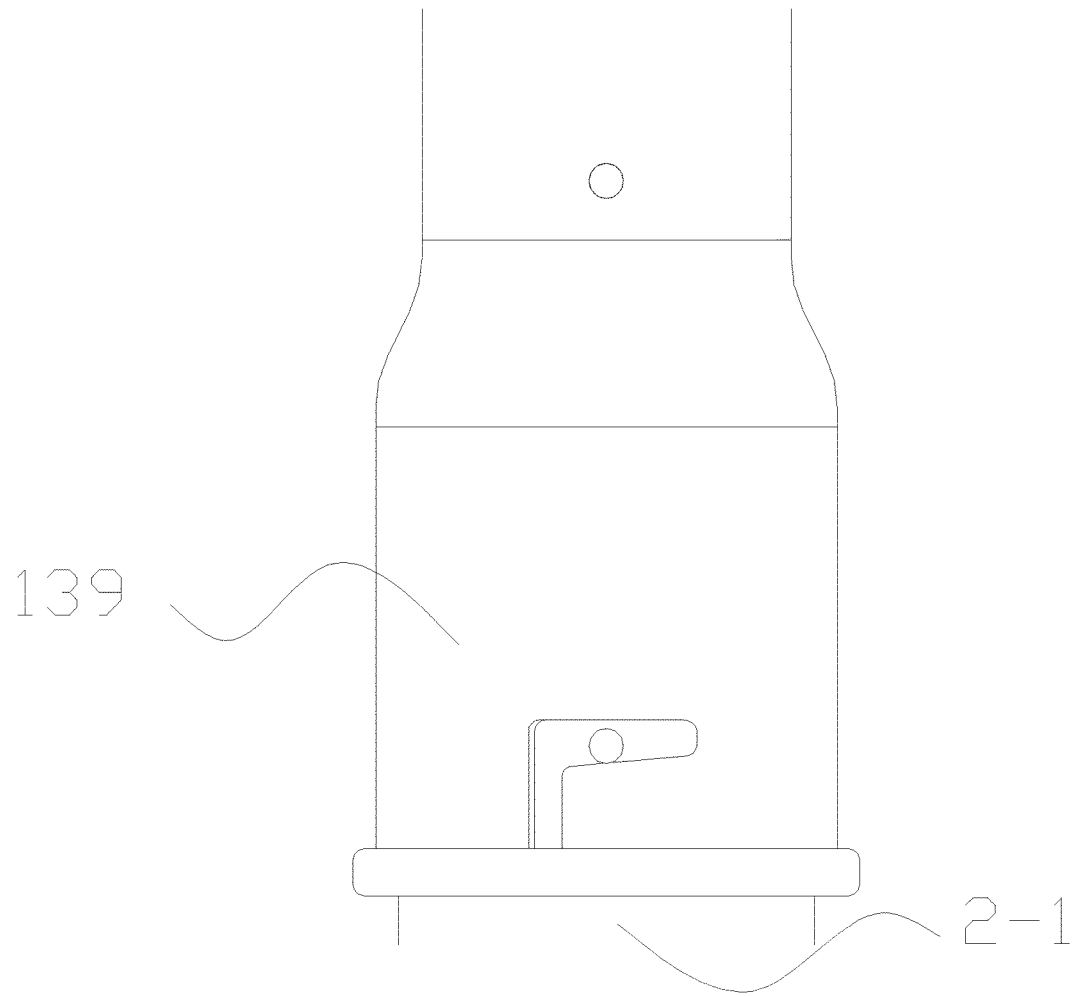
FIG. 6 shows a connection of a quick change interface of the handle and an end effector according to one embodiment of the invention.

FIG. 6 shows a connection of the quick change interface of the handle and an end effector.

As shown in FIG. 6, when the handle is connected to the end effector, the input terminal 2-1 slips into the precession sleeve 139, and meanwhile the precession pin of the input terminal 2-1 slips into the precession sleeve 139. The output head of the handle 137 slips into the power access of the input terminal 2-1. To tighten the precession sleeve 139, the precession pin of the input terminal 2-1 slips into the sloping chute of the precession sleeve 139, so that the handle is tightly connected to the end effector to transmit power.

Figure 7:
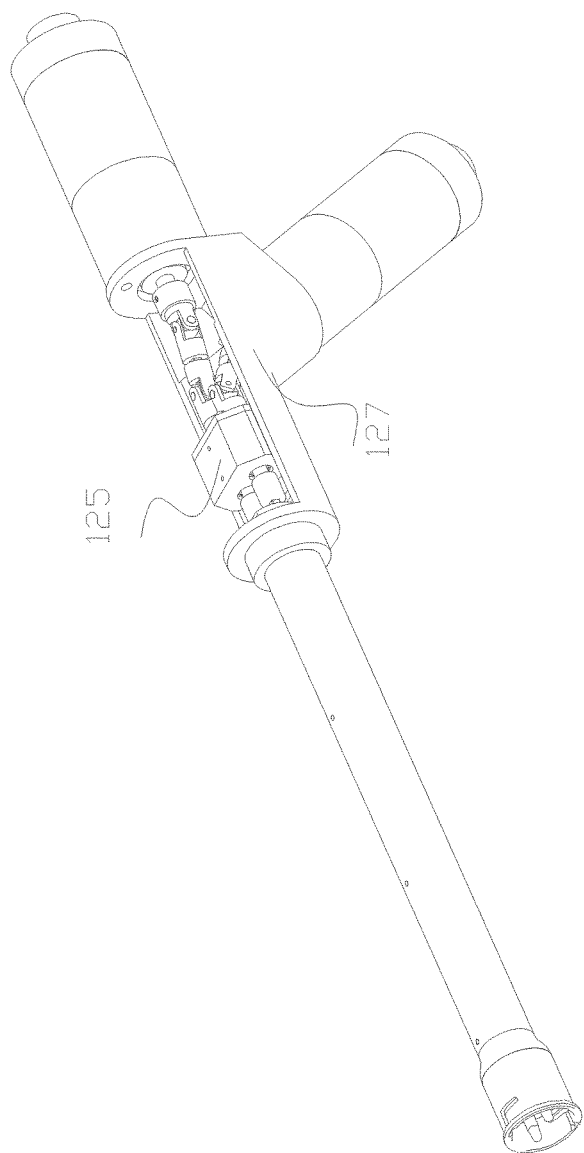
FIG. 7 is a mechanical drawing of a handle according to one embodiment of the invention.

FIG. 7 is a mechanical drawing of the handle.

As shown in FIG. 7, the bearing support 125 is fixed on the main frame 127.

Figure 8:
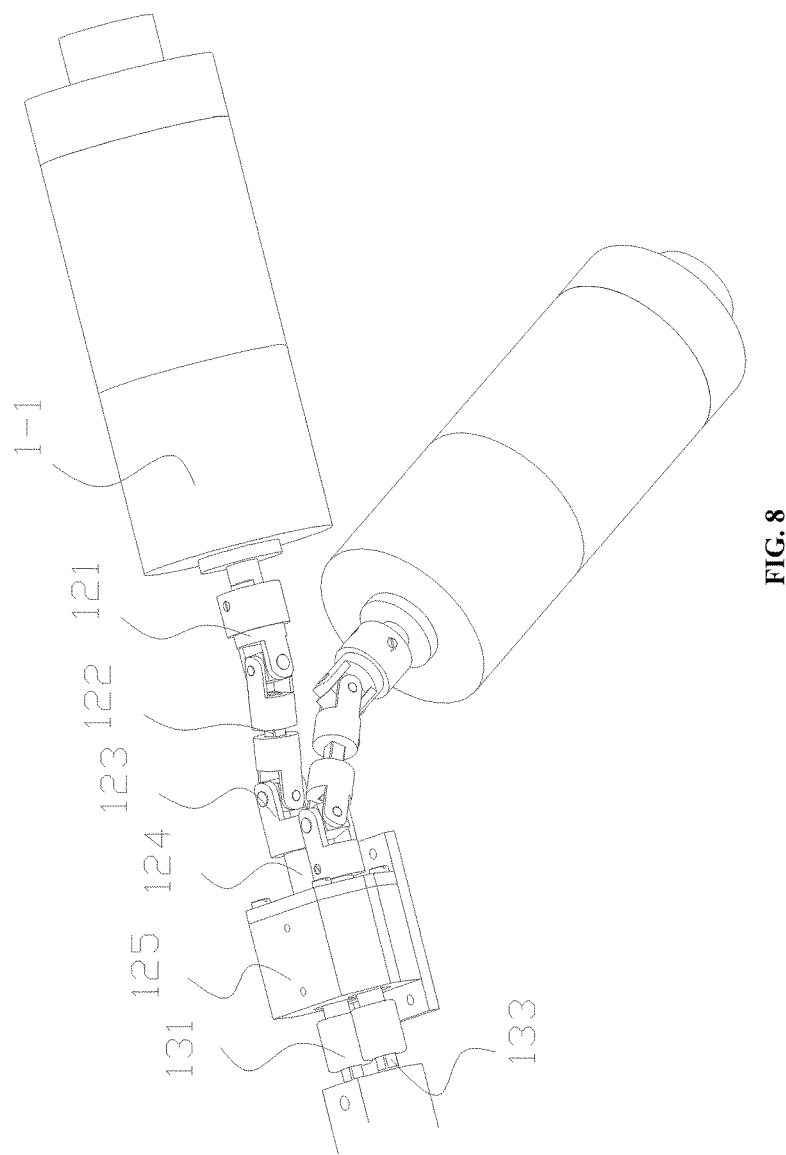
FIG. 8 is a schematic diagram of a power transmission mechanism of a handle according to one embodiment of the invention.

FIG. 8 is a schematic diagram of a power transmission mechanism of the handle.

As shown in FIG. 8, the power transmission mechanism 1-2 comprises two structural units and outputs two parallel transmitted rotations. The two structural units have the same structures, each comprising: a universal joint assembly, a bearing support, a drive shaft, a coupling, a drive flexible shaft, and an output head. The universal joint assembly comprises a first universal joint 121, a second universal joint 123, and a connection rod 122. The output shaft of the motor is connected to the first universal joint 121 using a tight pin or cylindrical pin. The first universal joint 121 is connected to the second universal joint 123 via the connection rod 122. The second universal joint 123 is connected to the drive shaft 124 using a tight pin or cylindrical pin. The drive shaft 124 is disposed in the bearing support 125. The drive shaft is supported by two bearings. The drive shaft 124 is connected to the drive flexible shaft 133 via the coupling 131. The drive flexible shaft 133 transmits the linear motion to the output head 137 of the handle. When the handle is connected to and fixed on the end effector 2 via the quick change interface, the output head 137 of the handle is connected to and supplies power for the input terminal.

The bearing support 125 comprises two bearings for supporting the drive shaft.

Optionally, the output shaft of the linear motor 1-1 is connected to the drive shaft 124 via a gear mechanism or a flexible shaft.

Figure 9:
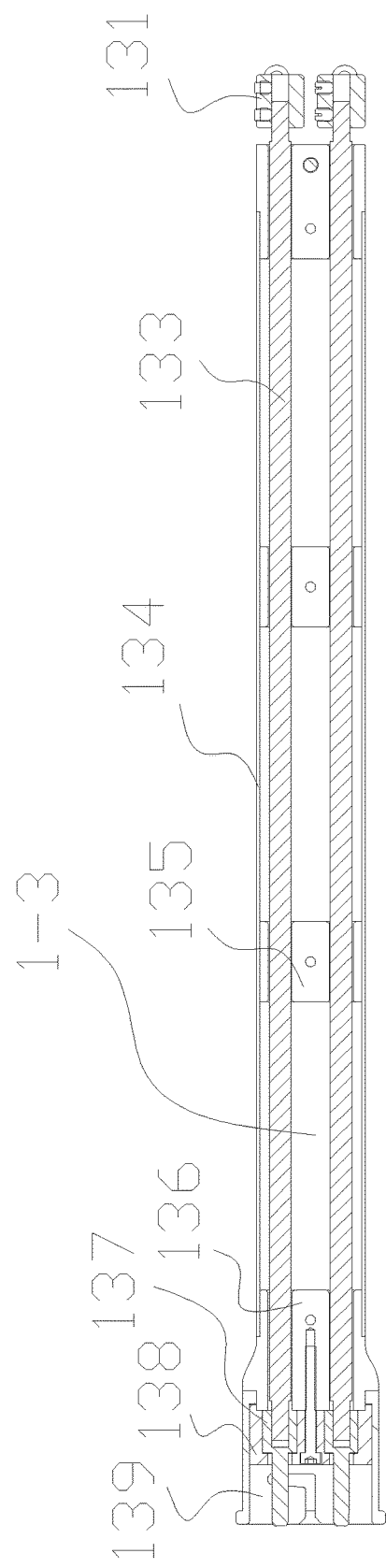
FIG. 9 shows an internal structure of a connection tube of a handle according to one embodiment of the invention.

FIG. 9 shows an internal structure of a connection tube of the handle.

As shown in FIGS. 8-9, the connection tube 1-3 of the handle is connected to the main frame of the power transmission mechanism 1-2. The drive flexible shaft 133 is connected to the drive shaft 124 of the power transmission mechanism 1-2 via the coupling 131. The drive flexible shaft 133 is disposed in the connection tube 134 and supported by a flexible shaft support 135. The flexible shaft support 135 is entirely fixed in the connection tube 134 using a pin, sleeve, connecting rod. The end joint 136 is fixed on the connection tube 134. The fixed seat 138 for the end joint is fixed on the end joint 136. The precession sleeve 139 is fixed between the fixed seat 138 and the end joint 136. The connection tube 134 is fixed on the main frame. The end joint 136 of the connection tube is fixed on the fixed seat 138 via a screw. The precession sleeve 139 is axially fixed and circumferentially rotatable. The precession sleeve 139 comprises a sloping chute. When the handle is connected to the end effector, the top of the connection pin of the end effector slips into the sloping chute of the precession sleeve, so that the output head of the handle is connected to the end effector and supplies power for the power transmission structure of the end effector.

Figure 10:
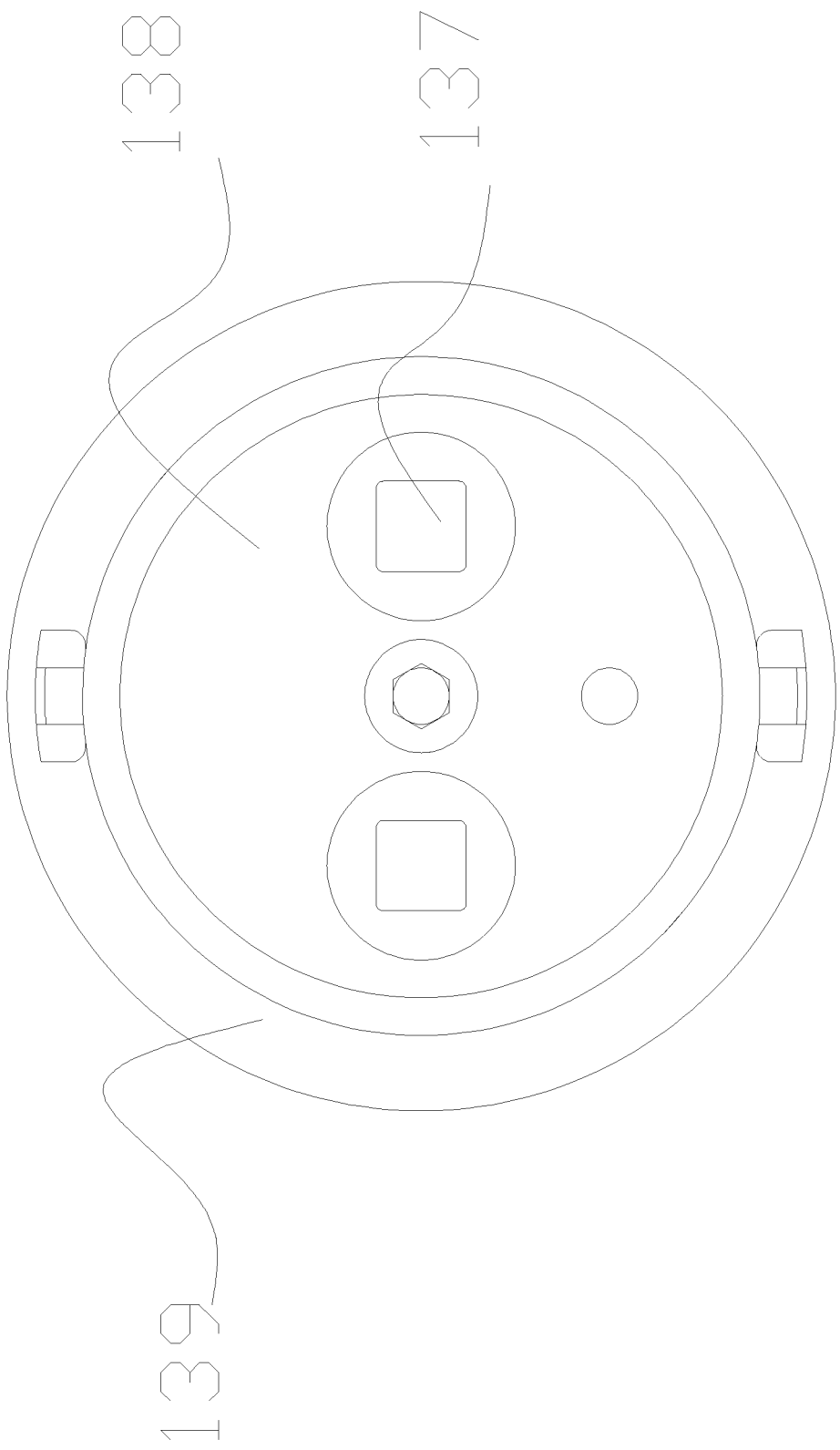
FIG. 10 is a front view of a quick change interface of a handle according to one embodiment of the invention.

FIG. 10 is a front view of a quick change interface of a handle.

As shown in FIG. 10, the precession sleeve 139 is disposed outside the fixed seat 138 through clearance fit. The output head 137 of the handle is disposed inside the fixed seat 138. When the handle is connected to the end effector 2, the output head of the handle is connected to the power input mechanism of the end effector, so that the linear motion from the linear motor 1-1 is transmitted to the end effector for surgery.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A handle for an electric surgical stapler, the electric surgical stapler comprising an end effector, the handle comprising a casing, a linear motor, a power transmission mechanism, and a quick change interface, wherein:
   the linear motor is disposed in the casing and configured to supply linear motion:
   the quick change interface is connected to the end effector;
   the power transmission mechanism comprises a driving flexible shaft, and the power transmission mechanism transmits the linear motion from the linear motor to the end effector via the driving flexible shaft;
   a drive module is disposed between the linear motor and the driving flexible shaft, and the power from the linear motor is transmitted to the driving flexible shaft via the drive module;
   the drive module comprises a universal joint assembly, a drive shaft, and a coupling;
   the universal joint assembly comprises a first universal joint, a second universal joint, and a connection rod;
   an output shaft of the linear motor is connected to the first universal joint, the first universal joint is connected to the connection rod, and the connection rod is connected to the second universal joint;
   the second universal joint is connected to the drive shaft; and
   the drive shaft is connected to the driving flexible shaft via the coupling.

2. A handle for an electric surgical stapler, the electric surgical stapler comprising an end effector, the handle comprising a casing, a linear motor, a power transmission mechanism, and a quick change interface, wherein:
   the linear motor is disposed in the casing and configured to supply linear motion:
   the quick change interface is connected to the end effector;
   the power transmission mechanism comprises a driving flexible shaft, and the power transmission mechanism transmits the linear motion from the linear motor to the end effector via the driving flexible shaft;
   a drive module is disposed between the linear motor and the driving flexible shaft, and the power from the linear motor is transmitted to the driving flexible shaft via the drive module;
   the drive module comprises a flexible shaft and a drive shaft; the linear motor is connected to the flexible shaft, the flexible shaft is connected to the drive shaft, and the drive shaft is connected to the driving flexible shaft.

3. The handle of claim 1, further comprising a connection tube, wherein one end of the connection tube is fixed on the casing, the other end thereof is connected to the quick change interface; and the driving flexible shaft is disposed in the connection tube.

4. A handle for an electric surgical stapler, the electric surgical stapler comprising an end effector, the handle comprising a casing, a linear motor, a power transmission mechanism, a quick change interface, and a connection tube, wherein:
   the linear motor is disposed in the casing and configured to supply linear motion:
   the quick change interface is connected to the end effector;
   the power transmission mechanism comprises a driving flexible shaft, and the power transmission mechanism transmits the linear motion from the linear motor to the end effector via the driving flexible shaft;
   one end of the connection tube is fixed on the casing, the other end thereof is connected to the quick change interface;
   the driving flexible shaft is disposed in the connection tube; and
   the connection tube is semirigid, and exhibits a certain bending deflection and rigidity under stress.

5. The handle of claim 3, wherein the connection tube is semirigid, and exhibits a certain bending deflection and rigidity under stress.

6. The handle of claim 4, wherein
   the connection tube comprises an end joint, the quick change interface comprises a fixed seat for the end joint, a precession sleeve, and an output head;
   the end joint is fixed on the connection tube; the fixed seat is fixed on the end joint of the connection tube; the precession sleeve is fixed between the fixed seat and the end joint, and is axially fixed and circumferentially rotatable; and the output head is disposed in the fixed seat, and is axially fixed and circumferentially rotatable; and
   one end of the output head is connected to the drive flexible shaft, and the other end thereof is connected to a transmission mechanism of the end effector.

7. The handle of claim 3, wherein
   the connection tube comprises an end joint, the quick change interface comprises a fixed seat for the end joint, a precession sleeve, and an output head;
   the end joint is fixed on the connection tube; the fixed seat is fixed on the end joint of the connection tube; the precession sleeve is fixed between the fixed seat and the end joint, and is axially fixed and circumferentially rotatable; and the output head is disposed in the fixed seat, and is axially fixed and circumferentially rotatable; and
   one end of the output head is connected to the drive flexible shaft, and the other end thereof is connected to a transmission mechanism of the end effector.

8. The handle of claim 4, wherein the quick change interface comprises a threaded connector, a snap spring, and a slip groove.

9. The handle of claim 3, wherein the quick change interface comprises a threaded connector, a snap spring, and a slip groove.

10. The handle of claim 1, wherein the electric surgical stapler is a linear stapler, circular anastomat, endoscopic stapler, or knife stapler.

* * * * *